(12) United States Patent
Yamada

(10) Patent No.: US 9,964,395 B2
(45) Date of Patent: May 8, 2018

(54) POSITION INDICATOR AND POSITION INDICATING METHOD

(71) Applicant: Wacom Co., Ltd., Saitama (JP)

(72) Inventor: Susumu Yamada, Gunma (JP)

(73) Assignee: Wacom Co., Ltd., Saitama (JP)

( * ) Notice: Subject to any disclaimer, the term of this patent is extended or adjusted under 35 U.S.C. 154(b) by 0 days. days.

(21) Appl. No.: 15/352,234

(22) Filed: Nov. 15, 2016

(65) Prior Publication Data
US 2017/0191818 A1   Jul. 6, 2017

(30) Foreign Application Priority Data
Jan. 6, 2016   (JP) .................................. 2016-000939

(51) Int. Cl.
| | | |
|---|---|---|
| G01B 7/004 | (2006.01) | |
| G01B 7/16 | (2006.01) | |
| G01N 17/00 | (2006.01) | |
| G06F 3/041 | (2006.01) | |
| G06F 3/046 | (2006.01) | |
| G06F 3/0354 | (2013.01) | |

(Continued)

(52) U.S. Cl.
CPC ............... G01B 7/004 (2013.01); G01B 7/18 (2013.01); G01N 17/00 (2013.01); G06F 3/03545 (2013.01); G06F 3/046 (2013.01); G06F 3/0416 (2013.01); *G01N 27/4162* (2013.01); *G01N 2030/645* (2013.01)

(58) Field of Classification Search
CPC ...... G01N 17/00; G01N 17/006; G01N 17/02; G01N 27/02; G01N 27/04; G01N 2030/345; G01N 2030/645; G01N 27/4162; G01L 1/10; G01L 1/20; G01L 1/22; G01R 27/00; G01B 7/004; G01B 7/18; G06F 3/03545

USPC .......... 324/76.11–76.83, 439, 459, 549, 600, 324/649, 691, 693, 697

See application file for complete search history.

(56) References Cited

U.S. PATENT DOCUMENTS

| | | |
|---|---|---|
| 7,149,647 B2 | 12/2006 | Katsurahira |
| 8,913,041 B2 | 12/2014 | Fukushima et al. |

(Continued)

FOREIGN PATENT DOCUMENTS

| | | |
|---|---|---|
| CN | 1485794 A | 3/2004 |
| JP | 2005-10844 A | 1/2005 |

(Continued)

OTHER PUBLICATIONS

Extended European Search Report, dated May 29, 2017, for corresponding European Application No. 16204207.1-1507, 10 pages.

*Primary Examiner* — Huy Q Phan
*Assistant Examiner* — Raul Rios Russo
(74) *Attorney, Agent, or Firm* — Seed Intellectual Property Law Group LLP

(57) ABSTRACT

A position indicator includes a resonant circuit configured to receive electromagnetic waves transmitted intermittently from a position detection device with a first duration and a second duration. The second duration is shorter than the first duration. The position indicator also includes a load resistance value control circuit configured to control a load resistance of the resonant circuit such that different values of the load resistance are set for the first duration and the second duration. A value of the load resistance set for the second duration is smaller than a value of the load resistance set for the first duration.

12 Claims, 10 Drawing Sheets

(51) Int. Cl.
G01N 30/64 (2006.01)
G01N 27/416 (2006.01)

(56) References Cited

U.S. PATENT DOCUMENTS

| | | | |
|---|---|---|---|
| 9,063,025 B2 | 6/2015 | Horie et al. | |
| 2005/0043918 A1* | 2/2005 | Katsurahira | G06F 1/3203 |
| | | | 702/178 |
| 2007/0205923 A1 | 9/2007 | Matsubara | |
| 2008/0257613 A1 | 10/2008 | Katsurahira | |
| 2010/0135049 A1* | 6/2010 | Radecker | H02M 3/33507 |
| | | | 363/21.03 |
| 2010/0142229 A1* | 6/2010 | Chen | H02M 3/33592 |
| | | | 363/21.02 |
| 2011/0215729 A1* | 9/2011 | Feldtkeller | H05B 41/2828 |
| | | | 315/224 |
| 2014/0239732 A1* | 8/2014 | Mach | H02J 5/00 |
| | | | 307/104 |
| 2015/0249484 A1* | 9/2015 | Mach | H02J 5/00 |
| | | | 307/104 |

FOREIGN PATENT DOCUMENTS

| | | |
|---|---|---|
| JP | 2011-186803 A | 9/2011 |
| JP | 2013-161307 A | 8/2013 |

* cited by examiner

FIG. 10 (Prior Art)
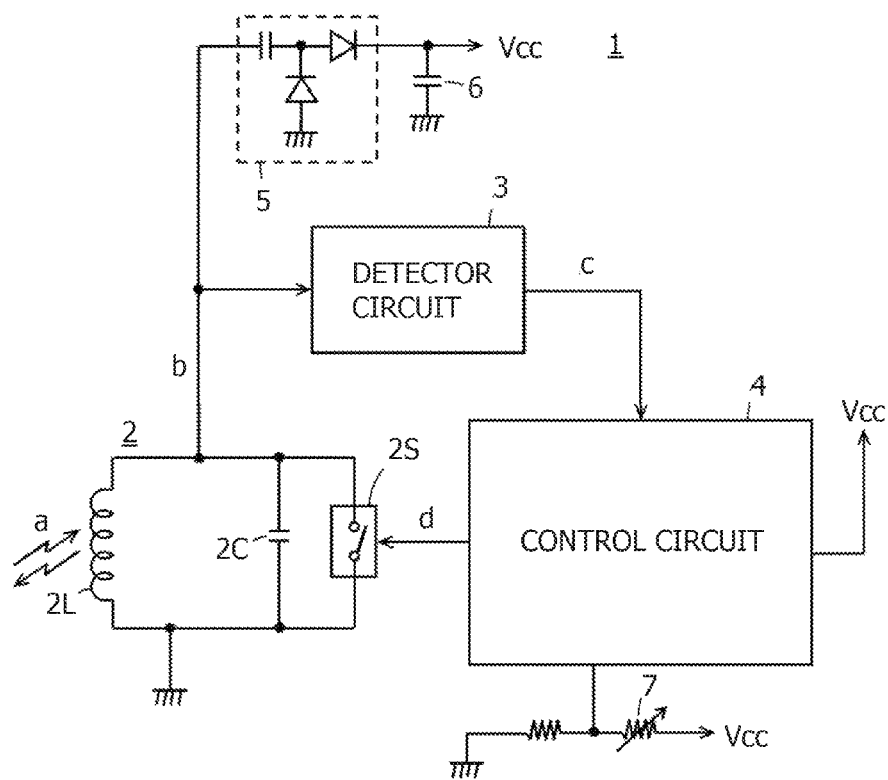
FIG. 11A (Prior Art)
FIG. 11B (Prior Art)
FIG. 11C (Prior Art)
FIG. 11D (Prior Art)

POSITION INDICATOR AND POSITION INDICATING METHOD

BACKGROUND

1. Technical Field

The present disclosure relates to a position indicator of an electromagnetic induction type which is used in conjunction with a position detection device that detects a position indicated by the position indicator using electromagnetic inductive coupling, and to a position indicating method.

2. Description of the Related Art

A position indicator of this type which is widely used today includes a resonant circuit formed by a parallel circuit composed of a coil and a capacitor, and is configured to return electromagnetic waves transmitted from a position detection device to the position detection device through the resonant circuit. In the position indicator of this type, the characteristics of the resonant circuit are often controlled in accordance with transmission data representing, for example, a pen pressure in synchronization with electromagnetic waves transmitted intermittently from the position detection device to return the transmission data representing, for example, the pen pressure to the position detection device (see, for example, Japanese Patent Laid-Open No. 2005-10844).

FIG. 10 is a diagram illustrating an exemplary configuration of the position indicator of this type, and FIGS. 11A to 11D are timing diagrams illustrating waveforms of signals at various portions of the position indicator having the exemplary configuration illustrated in FIG. 10.

A position indicator 1 illustrated in FIG. 10 includes a resonant circuit 2 formed by a parallel circuit composed of a coil 2L and a capacitor 2C connected in parallel. In the resonant circuit 2 according to this example, a switch 2S is connected in parallel with the coil 2L and the capacitor 2C. In this example, one end of the coil 2L of the resonant circuit 2 is grounded, while induction signals b (see FIG. 11B) based on electromagnetic waves a (see FIG. 11A) transmitted intermittently from a position detection device are obtained at an opposite end of the coil 2L.

Signals transmitted from the position detection device in the form of the electromagnetic waves a are alternating-current signals having a frequency equal to a resonance frequency of the resonant circuit 2 of the position indicator 1, and the alternating-current signals are made up of a signal (hereinafter referred to as a burst signal) which continues for 500 microseconds, for example, and data transmission synchronizing signals each of which continues for a period, e.g., 50 microseconds, shorter than the duration of the burst signal, and the number of which corresponds to the number of bits of transmission data representing, for example, a so-called pen pressure, i.e., a pressure applied to a tip portion (a pen point) of the position indicator 1, so that the transmission data can be transmitted by the position indicator 1. The data transmission synchronizing signals are synchronizing signals used when data is exchanged between the position indicator 1 and the position detection device, and are used, in the position detection device, to detect the transmission data from the position indicator 1 through sampling. In this case, the position detection device repeats a cycle of transmission of the burst signal and the subsequent data transmission synchronizing signals, the number of which is equal to the number of bits of the data transmitted from the position indicator 1.

The induction signals b obtained at the aforementioned opposite end of the coil 2L of the resonant circuit 2 due to the electromagnetic waves a transmitted from the position detection device are supplied to a detector circuit 3. In the detector circuit 3, envelope detection outputs for the induction signals b are each compared with a predetermined threshold value to generate a timing signal c (see FIG. 11C) which is synchronized with the electromagnetic waves a from the position detection device. The timing signal c generated in the detector circuit 3 is supplied to a control circuit 4, which is formed by, for example, a microprocessor.

The induction signal b obtained at the aforementioned opposite end of the coil 2L of the resonant circuit 2 is also supplied to and rectified by a rectifier circuit 5, and a charge storage capacitor 6 such as, for example, an electric double-layer capacitor, is charged with the rectified signal. The charge storage capacitor 6 forms a power supply circuit that generates a power supply voltage for driving the control circuit 4, and the control circuit 4 operates using an output voltage of the charge storage capacitor 6 as a power supply voltage Vcc.

The position indicator 1 illustrated in FIG. 10 includes a variable resistor 7 the resistance value of which varies in accordance with the pen pressure, and the control circuit 4 detects a voltage according to the resistance value of the variable resistor 7 to detect the pen pressure. Then, the control circuit 4 converts the detected pen pressure into multiple bits of digital data, and supplies a control signal d (see FIG. 11D) according to each bit ("0" or "1") of the digital data to the switch 2S to control the switch 2S to be turned on and off.

More specifically, in the example of FIG. 10, when a bit of the digital data, representing the pen pressure, is "1," the switch 2S is turned on to short both ends of the coil 2L so that electromagnetic wave energy stored in the coil 2L of the resonant circuit 2 disappears to cause no electromagnetic wave to be returned from the position indicator 1 to the position detection device. Meanwhile, when a bit of the digital data, representing the pen pressure, is "0," the switch 2S is kept in an OFF state to cause an electromagnetic wave to be returned from the position indicator 1 to the position detection device through the resonant circuit 2 composed of the coil 2L and the capacitor 2C. The digital data representing, for example, the pen pressure is thus subjected to amplitude shift keying (ASK) modulation or on-off keying (OOK) modulation, and is returned from the position indicator 1 to the position detection device.

In the position detection device, the electromagnetic waves subjected to the ASK modulation or the OOK modulation and returned from the position indicator 1 are sampled at a sampling timing based on the transmitted electromagnetic waves a, and when no electromagnetic wave is returned from the position indicator 1 at the sampling timing, the bit of the digital data is determined to be "1," and when the electromagnetic wave returned from the position indicator 1 at the sampling timing has a signal level equal to or higher than a predetermined threshold value, the bit of the digital data is determined to be "0." The digital data is thus demodulated.

As described above, the position indicator 1 illustrated in FIG. 10 generates the power supply voltage for driving the control circuit 4 from the electromagnetic waves transmitted from the position detection device, and also subjects the electromagnetic waves received from the position detection device to the ASK modulation or the OOK modulation using the digital data to be transmitted, and returns the modulated electromagnetic waves to the position detection device.

As described above, the position detection device repeatedly and cyclically transmits the alternating-current signals having a frequency equal to the resonance frequency of the resonant circuit 2 of the position indicator 1, that is, the burst signal which continues for a relatively long period, and the subsequent data transmission synchronizing signals each of which continues for a relatively short period and the number of which is equal to the number of bits of the transmission data to be transmitted from the position indicator 1. On the part of the position indicator 1, a charge storage capacitor 6 is charged primarily with the burst signal of the electromagnetic waves transmitted from the position detection device, and the data transmission synchronizing signals are subjected to the ASK modulation or the OOK modulation using the transmission data representing, for example, the pen pressure to transmit the transmission data to the position detection device.

Here, from the viewpoint of emphasizing the charging of the charge storage capacitor 6 in the position indicator 1, it is important to configure the resonant circuit 2 so as to minimize a loss of energy of the electromagnetic waves transmitted from the position detection device. Meanwhile, in view of transmitting the transmission data from the position indicator 1 to the position detection device, it is important to configure the position indicator 1 so as to be capable of increasing the speed of signal transmission in order to satisfy a recent demand for an increased number of bits of transmission data.

However, reducing the energy loss and increasing the speed of signal transmission are generally incompatible with each other, and to configure the resonant circuit of the position indicator so as to satisfy both the demands has been difficult so far.

In more detail, when the switch 2S is in the OFF state in FIG. 10, the resonant circuit 2 can be considered to have an infinitely large load resistance, and the resonant circuit 2 has a load resistor having a high resistance connected thereto. When the resonant circuit 2 thus has a large load resistance, an energy loss is small, but the resonant circuit 2 has a large resonance sharpness (Q), resulting in a reduction in the speed of signal transmission. Meanwhile, when the resonant circuit 2 has a small load resistance, the resonant circuit 2 has a small resonance sharpness (Q), which results in an increase in the speed of signal transmission, but a large energy loss occurs.

BRIEF SUMMARY

In view of the above circumstances, an object of the present disclosure is to provide a position indicator which is able to simultaneously satisfy both a demand for reducing the energy loss and a demand for increasing the speed of signal transmission, which are generally incompatible for the resonant circuit.

According to an embodiment of the present disclosure, there is provided a position indicator including a resonant circuit, and configured to return, to a position detection device, electromagnetic waves generated on a basis of electromagnetic waves transmitted intermittently from the position detection device with a first duration and a second duration shorter than the first duration, and received by the resonant circuit. The position indicator includes a load resistance value control circuit configured to control a value of load resistance of the resonant circuit such that different values of the load resistance are set for the first duration and the second duration, and the value of the load resistance set for the second duration is smaller than the value of the load resistance set for the first duration.

In the position indicator according to the above embodiment of the present disclosure, the value of the load resistance of the resonant circuit is made larger during a period in which an electromagnetic wave having the first duration is received than during a period in which an electromagnetic wave having the second duration shorter than the first duration is received. This reduces an energy loss during the period in which the electromagnetic wave having the first duration is received, which leads to an improvement in power receiving efficiency.

In addition, in the position indicator according to the above embodiment of the present disclosure, the value of the load resistance of the resonant circuit is made smaller during the period in which the electromagnetic wave having the second duration shorter than the first duration is received than during the period in which the electromagnetic wave having the first duration is received, and this leads to an increase in the speed of signal transmission. This makes it possible to increase the amount of information which is transmitted from the position indicator to the position detection device per unit time.

In the position indicator according to the above embodiment of the present disclosure, the value of the load resistance of the resonant circuit is controlled to vary in accordance with the first duration and the duration shorter than the first duration of the electromagnetic waves intermittently transmitted from the position detection device, whereby the demand for reducing the energy loss and the demand for increasing the speed of signal transmission, which are generally incompatible for the resonant circuit, can be simultaneously satisfied. Accordingly, the position indicator according to the above embodiment of the present disclosure is able to achieve both an improvement in efficiency of power reception from the position detection device via the electromagnetic waves, and an improvement in transmission rate of information transmitted from the position indicator to the position detection device.

BRIEF DESCRIPTION OF THE DRAWINGS

FIG. 10 is a diagram for explaining an example configuration of a known position indicator; and FIGS. 11A to 11D are diagrams used for explaining an operation of the known position indicator.

DETAILED DESCRIPTION

Hereinafter, a position indicator according to an embodiment of the present disclosure will be described with reference to the accompanying drawings.

Figure 1:
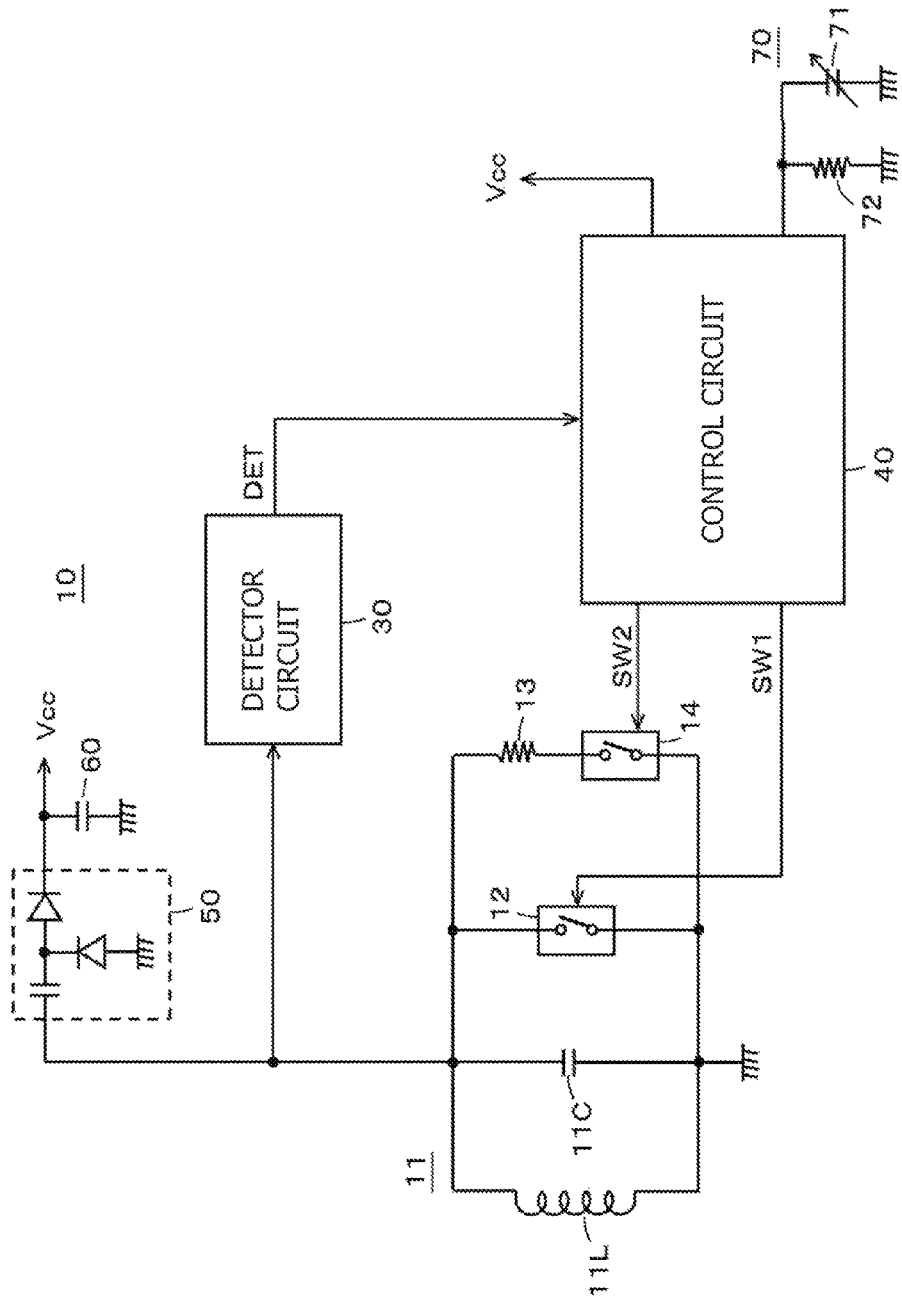
FIG. 1 is a diagram illustrating an example circuit configuration of a position indicator according to an embodiment of the present disclosure.

FIG. 1 illustrates an example circuit configuration of a position indicator 10 according to this embodiment. As illustrated in FIG. 1, the position indicator 10 according to this embodiment includes a resonant circuit 11 including a coil 11L and a capacitor 11C connected in parallel. In addition, in the position indicator 10 according to this embodiment, a switch circuit 12 is connected in parallel with the coil 11L and the capacitor 11C of the resonant circuit 11, and a series circuit which is composed of a resistor 13 and a switch circuit 14 connected in series and which forms a load resistance value control circuit is further connected in parallel with the coil 11L and the capacitor 11C of the resonant circuit 11.

The switch circuit 12 is controlled to be turned on and off in accordance with a switch control signal SW1 supplied from a control circuit 40, which will be described below, and if the switch circuit 12 is turned on, both ends of the coil 11L are shorted. That is, the switch circuit 12 is controlled to be turned on to cause electromagnetic wave energy stored in the coil 11L to disappear.

The switch circuit 14 is used to switch the value (i.e., a load resistance value) of load resistance of the resonant circuit 11, and is controlled to be turned on and off in accordance with a switch control signal SW2 supplied from the control circuit 40, which will be described below. More specifically, when the switch circuit 14 is in an OFF state, the load resistance value of the resonant circuit 11 is infinitely large, that is, is a large resistance value. Meanwhile, if the switch circuit 14 is turned on, the resistor 13 is connected in parallel with the resonant circuit 11, and the load resistance value of the resonant circuit 11 comes to be equal to a resistance value of the resistor 13, that is, a smaller value than when the switch circuit 14 is in the OFF state.

One end of the coil 11L of the resonant circuit 11 is grounded, while induction signals of electromagnetic waves transmitted intermittently from a position detection device are obtained at an opposite end of the coil 11L. The induction signals obtained at the opposite end of the coil 11L of the resonant circuit 11 are supplied to a detector circuit 30, and are subjected to an envelope detection process in the detector circuit 30, so that an envelope detection output DET of each induction signal is obtained from the detector circuit 30. The envelope detection output DET obtained from the detector circuit 30 is supplied to the control circuit 40.

In this embodiment, the control circuit 40 is formed by a microprocessor unit, and the switch control signal SW2, which is used to control switching of the switch circuit 14, is generated from the envelope detection output DET supplied from the detector circuit 30. In addition, the control circuit 40 generates the switch control signal SW1, which is used to control switching of the switch circuit 12, on the basis of transmission data and the envelope detection output DET supplied from the detector circuit 30 in this embodiment.

The transmission data is generated in the control circuit 40 in the following manner. That is, in this embodiment, a pen pressure detection circuit 70 is connected to the control circuit 40. In the position indicator 10 according to this embodiment, a variable capacitor 71 the capacitance of which varies in accordance with pen pressure is used as a pen pressure detection section, and the pen pressure detection circuit 70 is made up of the variable capacitor 71 and a resistor 72 connected in parallel. Examples of the pen pressure detection section which can be used include: a variable capacitor the capacitance of which varies in accordance with the pen pressure and which uses a well-known pen pressure detection mechanism as described in, for example, Japanese Patent Laid-Open No. 2011-186803; and a variable capacitor which uses a semiconductor device and the capacitance of which varies in accordance with the pen pressure as disclosed in, for example, Japanese Patent Laid-Open No. 2013-161307.

The control circuit 40 charges the variable capacitor 71 up to a predetermined potential, and thereafter causes the variable capacitor 71 in a charged voltage condition to discharge through the resistor 72, and measures a time T until the variable capacitor 71 reaches a predetermined threshold voltage. The time T measured depends on the capacitance of the variable capacitor 71 at the time, and therefore, a pen pressure which is being applied to the position indicator 10 is detected from the time T. The control circuit 40 then converts the detected pen pressure into multiple bits of digital data, which are the transmission data, and holds the multiple bits of digital data. Note that the transmission data is not limited to information as to the pen pressure, and that examples of the transmission data include information as to the state of a side switch provided on the position indicator 10, identification information of the position indicator 10 stored in a memory provided in the position indicator 10, and so on, some combination of the above, and all of the above.

The control circuit 40 generates the switch control signal SW1, which is used to control the switching of the switch circuit 12, from the value of each bit of the generated transmission data and the envelope detection output DET supplied from the detector circuit 30. In the related-art position indicator 1 described above in the Description of the Related Art, the switch circuit 2S is turned on or off in accordance with the value of each bit of the generated transmission data, and is kept in an ON state for a predetermined time when the value of the bit of the transmission data is "1." In the position indicator 10 according to this embodiment, the switch circuit 12 is similarly kept in the ON state for a predetermined time when the value of the bit of the generated transmission data is "1," and the transmission data is thus transmitted (returned) to the position detection device in the form of an ASK modulation signal or an OOK modulation signal.

Further, in the position indicator 10 according to this embodiment, the envelope detection output DET supplied from the detector circuit 30 is monitored, and even when the value of a bit of the transmission data is "0," the switch circuit 12 is turned on at a predetermined timing and kept in the ON state for a predetermined time to shorten a bit period of the transmission data, as described below.

The induction signal obtained at the opposite end of the coil 11L of the resonant circuit 11 is also supplied to and rectified by a rectifier circuit 50, and a charge storage capacitor 60, such as, for example, an electric double-layer capacitor, is charged with the rectified signal. The charge storage capacitor 60 forms a power supply circuit that generates a power supply voltage for driving the control circuit 40. The control circuit 40 operates using an output voltage of the charge storage capacitor 60 as a power supply voltage Vcc.

The control circuit 40, the switch circuit 12, the switch circuit 14, and the resistor 13 together form a resonance characteristic control circuit. That is, the resonance characteristics of the resonant circuit 11 are controlled by controlling the switching of the switch circuit 12 with the switch control signal SW1 supplied from the control circuit 40 and the switching of the switch circuit 14 with the switch control signal SW2 supplied from the control circuit 40.

Figure 2:
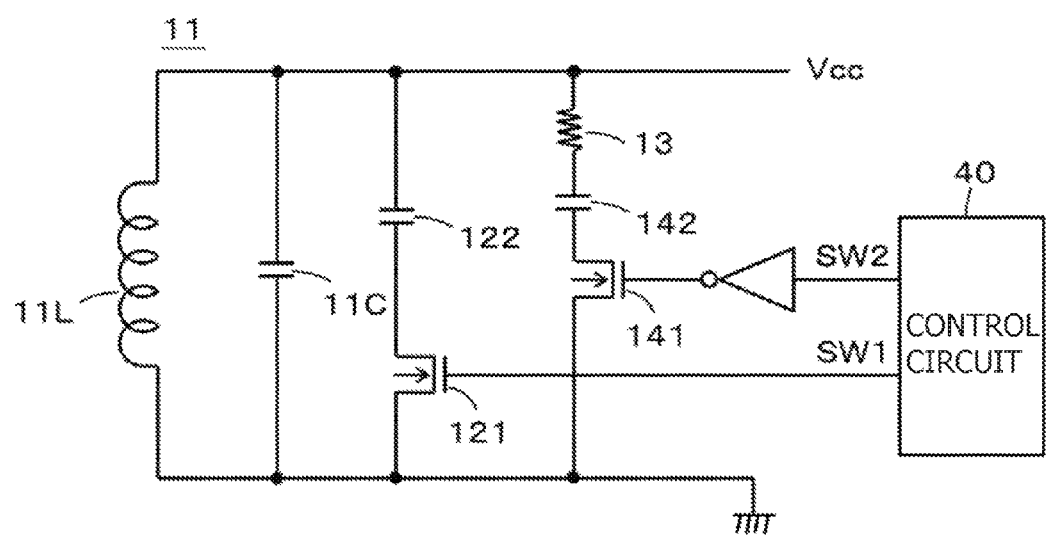
FIG. 2 is a diagram illustrating a portion of the example circuit configuration illustrated in FIG. 1.

FIG. 2 illustrates an exemplary practical configuration of the resonance characteristic control circuit. Specifically, in the example of FIG. 2, the switch circuit 12 is formed by a transistor 121, and a capacitor 122, which is used to prevent a shift of a negative potential at the time of switching, is connected in series with a source and a drain of the transistor 121. The switch control signal SW1 is supplied from the control circuit 40 to a gate of the transistor 121.

Meanwhile, the switch circuit 14 is formed by a transistor 141, and similarly, a capacitor 142, which is used to prevent a shift of a negative potential at the time of switching, is connected in series with a source and a drain of the transistor 141 and the resistor 13. The switch control signal SW2 is supplied from the control circuit 40 to a gate of the transistor 141.

Figure 3:
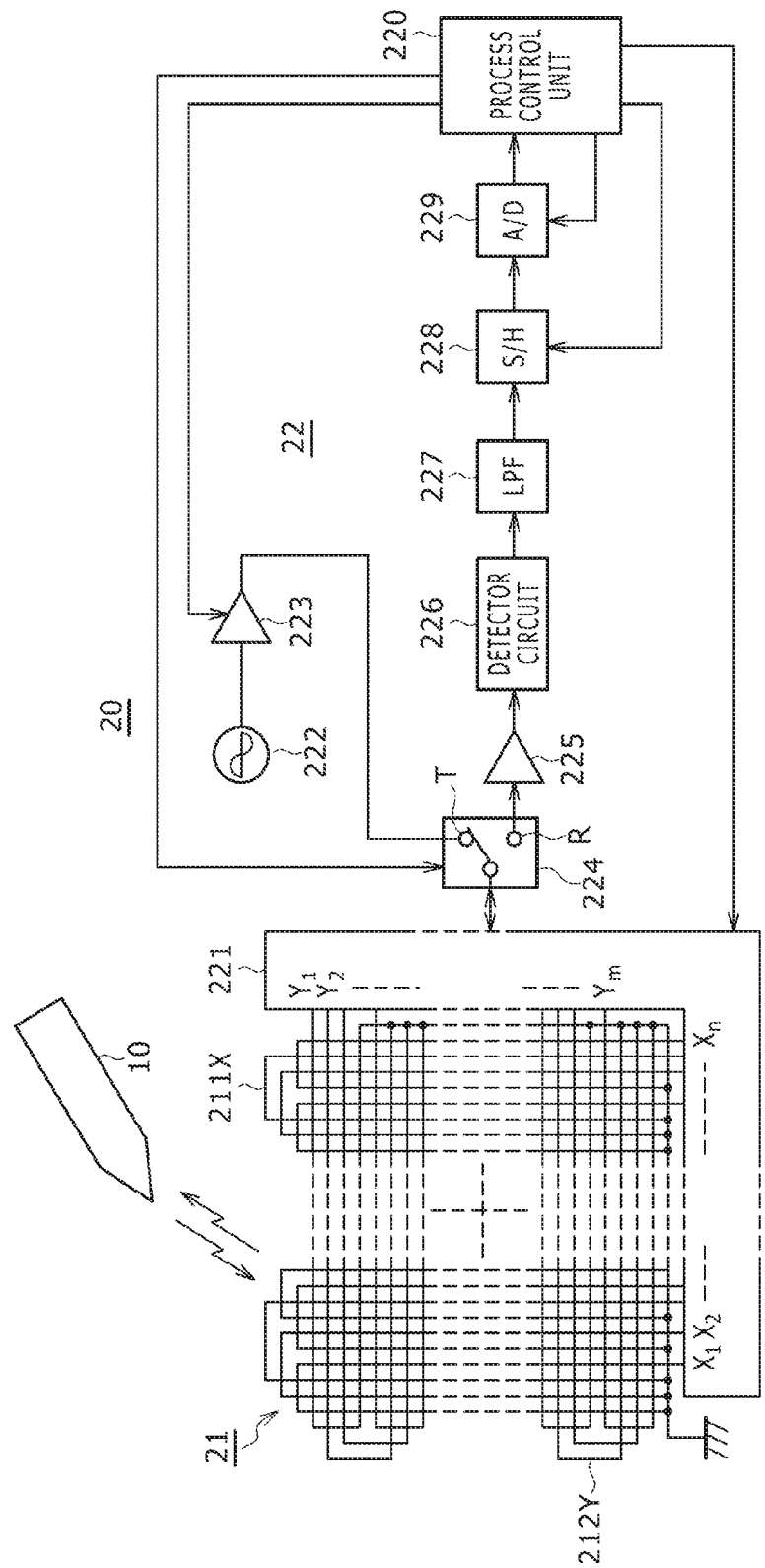
FIG. 3 is a diagram illustrating an exemplary structure of a position detection device used in conjunction with the position indicator according to an embodiment of the present disclosure.

Next, an exemplary structure of the position detection device, which is used in conjunction with the position indicator 10 according to this embodiment, will now be described below. FIG. 3 is a diagram illustrating an exemplary structure of a position detection device 20 of an electromagnetic induction type used in conjunction with the position indicator 10 according to this embodiment.

The position detection device 20 according to this embodiment includes a position detection sensor 21. As illustrated in FIG. 3, in the position detection sensor 21, a plurality of rectangular x-axis direction loop coils 211X, which form x-axis direction loop coil group conductors, are arranged at regular intervals in a horizontal direction (i.e., an x-axis direction) of a detection area for the position indicated by the position indicator 10 such that the x-axis direction loop coils 211X sequentially overlap with one another. In addition, a plurality of rectangular y-axis direction loop coils 212Y, which form y-axis direction loop coil group conductors, are arranged at regular intervals in a vertical direction (i.e., a y-axis direction) perpendicular to the horizontal direction of the detection area for the position indicated by the position indicator 10 such that the y-axis direction loop coils 212Y sequentially overlap with one another. In this embodiment, n x-axis direction loop coils 211X are arranged in the x-axis direction, while m y-axis direction loop coils 212Y are arranged in the y-axis direction.

In addition, a sensor circuit 22 is connected to the position detection sensor 21. The sensor circuit 22 includes a selection circuit 221, an oscillator 222, a current driver 223, a transmission/reception switching circuit 224, a receiving amplifier 225, a detector circuit 226, a low-pass filter 227, a sample and hold circuit 228, an analog-to-digital (A/D) conversion circuit 229, and a process control unit 220.

Each of the x-axis direction loop coils 211X and the y-axis direction loop coils 212Y is connected to the selection circuit 221. The selection circuit 221 selects the x-axis direction loop coils 211X and the y-axis direction loop coils 212Y one after another in accordance with control instructions from the process control unit 220.

The oscillator 222 generates an alternating-current signal at a frequency of f0, which is equal to a resonance frequency of the resonant circuit 11 of the position indicator 10. The alternating-current signal is supplied to the current driver 223, is converted to an electric current therein, and is thereafter sent to the transmission/reception switching circuit 224. Under control of the process control unit 220, the transmission/reception switching circuit 224 switches the destination to which the loop coil 211X or 212Y selected by the selection circuit 221 is connected between a transmission-side terminal T and a reception-side terminal R each time a predetermined time period elapses. The current driver 223 is connected to the transmission-side terminal T, while the receiving amplifier 225 is connected to the reception-side terminal R.

Therefore, at the time of transmission, the alternating-current signal is supplied from the current driver 223 to the loop coil 211X or 212Y selected by the selection circuit 221 via the transmission-side terminal T of the transmission/reception switching circuit 224. At the time of transmission, the process control unit 220 controls the current driver 223 so that the alternating-current signals will be intermittently transmitted with two types of durations as illustrated in FIG. 4A and FIG. 5A.

FIGS. 5A to 5G are timing diagrams for explaining an operation of the position indicator 10 according to this embodiment. Meanwhile, FIGS. 4A to 4F are timing diagrams illustrating the case where the switch circuit 12 is controlled on the basis of the transmission data as in related art while a switching control operation in connection with the switch circuit 14 is performed in the same manner as in the case of FIGS. 5A to 5G. FIGS. 4A to 4F are to be compared with FIGS. 5A to 5G to make an advantageous effect of the position indicator 10 according to this embodiment clearer.

Figure 4:
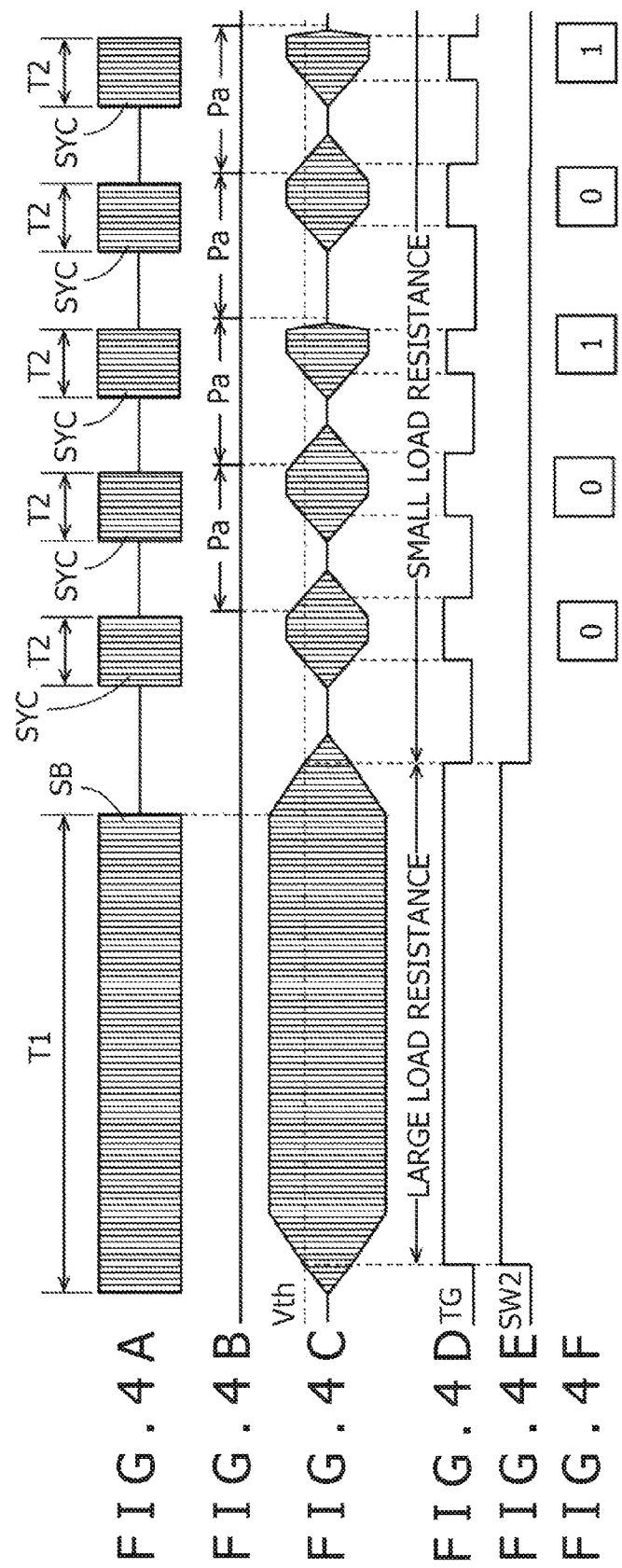
FIGS. 4A to 4F are diagrams used for explaining an operation of the position indicator according to an embodiment of the present disclosure.
Figure 5:
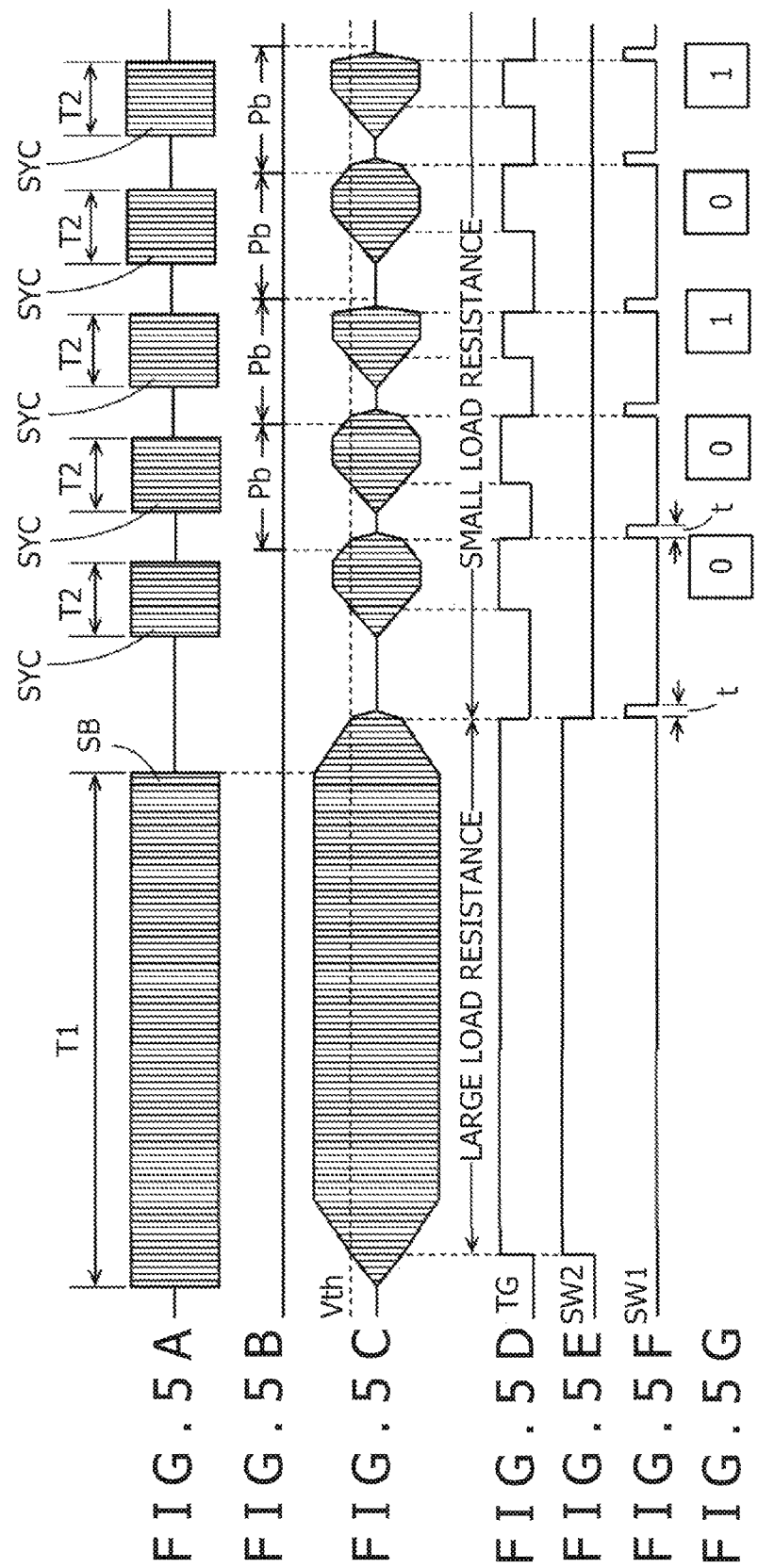
FIGS. 5A to 5G are diagrams used for explaining the operation of the position indicator according to an embodiment of the present disclosure.

In this example, as illustrated in FIG. 4A and FIG. 5A, transmission signals from the position detection device 20 are made up of a burst signal SB having a first duration T1, which is relatively long and is, for example, 500 microseconds, and a plurality of data transmission synchronizing signals SYC each having a second duration T2 (T2<T1), which is relatively short and is, for example, 50 microseconds. The number of data transmission synchronizing signals SYC each having the second duration T2 is equal to the number of bits of the transmission data transmitted from the position indicator 10. The position detection device 20 repeats an operation of transmitting one burst signal SB and then the data transmission synchronizing signals SYC equal in number to the bits of the transmission data transmitted from the position indicator 10. In other words, one cycle is composed of transmission of one burst signal SB and a plurality of data transmission synchronizing signals SYC, and the position detection device 20 repeats this cycle.

As illustrated in FIG. 4B and FIG. 5B, the process control unit 220 of the position detection device 20 decodes the transmission data from the position indicator 10 on the basis of a reception signal of the transmission data with a sampling point set at a timing point a little time after an end of the duration T2 of each data transmission synchronizing signal SYC. Each of a period Pa shown in FIG. 4B and a period Pb shown in FIG. 5B is a transmission period of the data transmission synchronizing signal SYC, that is, a transmission period (i.e., a bit period) of the bit of the transmission data from the position indicator 10.

The burst signal SB and the data transmission synchronizing signals SYC as described above are, in the form of electromagnetic waves, transmitted from the position detection device 20 to the position indicator 10. The position indicator 10 receives the electromagnetic waves at the resonant circuit 11. Then, the position indicator 10 performs a process as described below using the resonance characteristic control circuit, and returns signals in the form of electromagnetic waves from the resonant circuit 11 to the position detection device 20. Here, FIG. 4C and FIG. 5C illustrate example waveforms of the electromagnetic waves returned from the position indicator 10 to the position detection device 20.

When the electromagnetic wave returned from the position indicator 10 is received by the position detection device 20, an induced voltage generated in the loop coil 211X or 212Y selected by the selection circuit 221 is supplied to the receiving amplifier 225 via the selection circuit 221 and the reception-side terminal R of the transmission/reception switching circuit 224, and is amplified by the receiving amplifier 225, and the resultant signal is sent to the detector circuit 226. In the transmission/reception switching circuit 224, the transmission-side terminal T is selected in the first half of a period during which each one of the loop coils 211X and 212Y is selected by the selection circuit 221, and the reception-side terminal R is selected in the second half of the period.

The detector circuit 226 detects the signal sent from the receiving amplifier 225, and the detected output signal is supplied to the A/D conversion circuit 229 via the low-pass filter 227 and the sample and hold circuit 228. The A/D conversion circuit 229 converts the analog signal to a digital signal, and supplies the resulting digital signal to the process control unit 220.

In a period of the duration T1 of the burst signal SB, the process control unit 220 performs control for detecting the position indicated by the position indicator 10. More specifically, the process control unit 220 controls the selection of the loop coils 211X and 212Y in the selection circuit 221, the signal switching in the transmission/reception switching circuit 224, timing in the sample and hold circuit 228, and so on.

The process control unit 220 controls the transmission/reception switching circuit 224 to switch to the transmission-side terminal T to energize the loop coil 211X or 212Y selected by the selection circuit 221 to send an electromagnetic wave. The resonant circuit 11 of the position indicator 10, which is made up of the coil 11L and the capacitor 11C, receives the electromagnetic wave sent from the loop coil 211X or 212Y, and stores energy.

Next, the process control unit 220 controls the transmission/reception switching circuit 224 to switch to the reception-side terminal R. An electromagnetic wave returned from the position indicator 10 causes an induced voltage corresponding to the distance from the position indicator 10 to be generated in each of the loop coils 211X and 212Y of the x-axis direction loop coil group and the y-axis direction loop coil group, and the process control unit 220 detects the level of the induced voltage.

On the basis of the level of the voltage value of the induced voltage generated in each of the loop coils 211X and 212Y, the process control unit 220 calculates a coordinate value of the position indicated by the position indicator 10 in the detection area of the position detection sensor 21 with respect to the x-axis direction and the y-axis direction.

Then, after an end of the period of the duration T1 of the burst signal SB, the process control unit 220 performs a process of receiving data transmitted from the position indicator 10. In this case, if the position indicated by the position indicator 10 has been detected in the period of the duration T1 of the burst signal SB, the process control unit 220 controls the selection circuit 221 to select a loop coil 211X or 212Y near the detected position.

Then, the process control unit 220 samples a reception level of the electromagnetic wave returned from the position indicator 10 at the sampling point of the reception signal of the transmission data from the position indicator 10 shown in FIG. 4B and FIG. 5B.

In this case, as described above with reference to FIGS. 10 and 11, the resonance characteristic control circuit of the position indicator 10 is controlled to return the electromagnetic wave of the data transmission synchronizing signal SYC received from the position detection device 20 through the resonant circuit 11 when the value of the bit of the transmission data is "0," and not to return the electromagnetic wave when the value of the bit of the transmission data is "1."

The position detection device 20 receives the electromagnetic wave returned from the position indicator 10, and the reception level of the electromagnetic wave returned from the position indicator 10 at the sampling point of the reception signal of the transmission data from the position indicator 10 is high when the value of the bit is "0," and low (zero) when the value of the bit is "1," as shown in FIGS. 4B and 4C and FIGS. 5B and 5C, and thus, the transmission data from the position indicator 10 as shown in FIG. 4F and FIG. 5G can be decoded.

In the position indicator 10 according to this embodiment, the resonance characteristic control circuit is formed by the control circuit 40, the switch circuit 12, the switch circuit 14, and the resistor 13 as described above, and not only the switch circuit 12 is controlled to be turned on and off in accordance with the value of the bit of the transmission data described above, but also control of switching the load resistance value of the resonant circuit 11 and a controlling process for improving the transmission rate of the transmission data are performed.

An operation of the position indicator 10 according to this embodiment will now be further described below with reference to flowcharts of FIGS. 6, 7, 8, and 9, with focus placed on the controlling process by the resonance characteristic control circuit. In the following description, it is assumed that a process of each step in the flowcharts of FIGS. 6 to 9 is performed by the control circuit 40.

The control circuit 40 of the position indicator 10 first monitors the reception of the electromagnetic wave from the position detection device 20 (step S101), and determines whether electromagnetic coupling has been established so that the electromagnetic wave from the position detection device 20 can be received with a signal level equal to or higher than a predetermined level (step S102). At this time, the switch circuit 12 is kept in the OFF state, and the switch circuit 14 is also kept in the OFF state to allow the load resistance value of the resonant circuit 11 to be large (theoretically, infinitely large).

If it is determined at step S102 that electromagnetic coupling has not been established in relation to the position detection device 20, the control circuit 40 returns control to step S101. Meanwhile, if it is determined at step S102 that electromagnetic coupling has been established in relation to the position detection device 20, the control circuit 40 determines whether a rise of an induction signal of the electromagnetic wave from the position detection device 20 obtained at the resonant circuit 11 has been detected (step S103).

In this embodiment, the control circuit 40 compares the envelope detection output DET from the detector circuit 30 with a predetermined threshold level Vth, and determines that a rise of the burst signal SB or the data transmission synchronizing signal SYC has been detected when an increase of the envelope detection output DET beyond the threshold level Vth has been detected, and determines that a fall of the burst signal SB or the data transmission synchronizing signal SYC has been detected when a decrease of the envelope detection output DET beyond the threshold level Vth has been detected. In addition, the control circuit 40 discriminates between the burst signal SB and the data transmission synchronizing signal SYC by identifying the duration of the alternating-current signal at a frequency of f0 from the envelope detection output DET from the detector circuit 30.

Next after step S103, it is determined whether the duration of the alternating-current signal is longer than a predetermined value, that is, the duration of the data transmission synchronizing signal SYC (step S104). If it is determined at step S104 that the duration of the alternating-current signal is not longer than the predetermined value, the control circuit 40 returns control to step S103.

If it is determined at step S104 that the duration of the alternating-current signal is longer than the predetermined value, the control circuit 40 recognizes that the alternating-current signal identified is a section of a burst signal SB, and waits for a fall of the burst signal SB (step S105). Then, if it is determined at step S105 that a fall of the burst signal SB has been detected, the control circuit 40 issues the switch control signal SW2 to turn on the switch circuit 14 to cause the resistor 13 to become a load resistor of the resonant circuit 11. That is, the load resistance value of the resonant circuit 11 is switched to a value smaller than the load resistance value in the period of the duration T1 of the burst signal SB (step S106).

As shown in FIG. 4E and FIG. 5E, the switch control signal SW2 supplied from the control circuit 40 to the switch circuit 14 is kept at a high level during a period corresponding to the duration T1 of the burst signal SB, and is kept a low level in a remaining period. This results in a large load resistance value of the resonant circuit 11 during the period corresponding to the duration T1 of the burst signal SB, allowing the resonant circuit 11 to receive the electromagnetic wave from the position detection device 20 with limited energy loss, and allowing the charge storage capacitor 60 to be charged through the rectifier circuit 50.

In a period of the multiple data transmission synchronizing signals SYC subsequent to the period corresponding to the duration T1 of the burst signal SB, the load resistance value of the resonant circuit 11 is smaller than in the period corresponding to the duration T1 of the burst signal SB, and therefore, transmission of the transmission data is possible with a shorter period Pa (see FIG. 4B) than in the case of the known position indicator 1 described above with reference to FIG. 10 and FIGS. 11A to 11D.

Specifically, in the case of the known position indicator 1 described above with reference to FIG. 10 and FIGS. 11A to 11D, the load resistance value of the resonant circuit 2 is large, as the load resistance value of the resonant circuit 11 is large when the switch circuit 14 is in the OFF state in the position indicator 10 according to this embodiment. The period of the data transmission synchronizing signal SYC needs to be set so that a signal in a falling region of the data transmission synchronizing signal SYC disappears before a point in time at which the next data transmission synchronizing signal SYC rises, and a stable condition is established before the point in time at which the data transmission synchronizing signal SYC rises. However, in the case where the load resistance value of the resonant circuit 2 is large, the signal in the falling region of the data transmission synchronizing signal SYC remains for a long time, and a long period of the data transmission synchronizing signal SYC is accordingly set.

In contrast, in the position indicator 10 according to this embodiment, the load resistance value of the resonant circuit 11 is set to be smaller in the period of the multiple data transmission synchronizing signals SYC than in the period corresponding to the duration T1 of the burst signal SB to allow a duration of the signal in the falling region of the data transmission synchronizing signal SYC to be made shorter, allowing an improvement in signal transmission rate. Therefore, in a system including a combination of the position detection device 20 and the position indicator 10 according to this embodiment, the period Pa of the data transmission synchronizing signal SYC can be made shorter than in the case of a system using the known position indicator 1 as described above with reference to FIG. 10 and FIGS. 11A to 11D.

Moreover, the position indicator 10 according to this embodiment is configured so that the period of each of the multiple data transmission synchronizing signals SYC can be made even shorter than the period Pa, as described below.

Before an operation of the position indicator 10 according to this embodiment in the period of the multiple data transmission synchronizing signals SYC after the duration T1 of the burst signal SB (the operation illustrated in the timing diagram of FIGS. 5A to 5G) is described, the operation illustrated in the timing diagram of FIGS. 4A to 4F, which is similar to an operation in the period of the data transmission synchronizing signals SYC in related art, will now be described below for the sake of comparison.

In this case, once a rise of the data transmission synchronizing signal SYC is detected, the control circuit 40 refers to a bit of the transmission data to be transmitted with the data transmission synchronizing signal SYC held in a buffer memory (see FIG. 4F).

Then, if the bit of the transmission data referred to is "1," the control circuit 40 detects a start of a fall of the data transmission synchronizing signal SYC from the envelope detection output DET, and controls the switch circuit 12 to be turned on and kept in the ON state for a predetermined time t after the detected start of the fall such that energy of the data transmission synchronizing signal SYC stored in the resonant circuit 11 disappears to cause no returned electromagnetic wave to be detected at the sampling point of reception data in the position detection device 20 (see the third and fifth data transmission synchronizing signals SYC in FIGS. 4B and 4C). Here, the predetermined time t, for which the switch circuit 12 is kept in the ON state, is a time sufficient to cause the energy of the data transmission synchronizing signal SYC stored in the resonant circuit 11 to disappear, which may be relatively short, and after the predetermined time t elapses, the switch circuit 12 is returned to the OFF state.

Meanwhile, if the bit of the transmission data referred to is "0," the control circuit 40 does not control the switch circuit 12, allowing the electromagnetic wave of the data transmission synchronizing signal SYC to be returned as it is to the position detection device 20 through the resonant circuit 11 (see the first, second, and fourth data transmission synchronizing signals SYC in FIG. 4C).

In contrast, as illustrated in FIGS. 5A to 5G, in the position indicator 10 according to this embodiment, the control circuit 40 forcibly reduces the signal level of a signal in the falling region of each data transmission synchronizing signal SYC, preferably to zero, at a point in time after the sampling point, in the position detection device 20, of the reception signal of the transmission data from the position indicator 10, even when the bit of the transmission data is "0." This allows the period of the data transmission synchronizing signal SYC to be the period Pb, which is still shorter than the period Pa. In addition, in the position indicator 10 according to this embodiment, the signal level of a signal in a falling region of the burst signal SB is also forcibly reduced to further increase the speed of data transmission.

In the case of this example, a timing point at which the signal level of the signal in the falling region of each of the multiple data transmission synchronizing signals SYC is forcibly reduced is set at a point in time after the reception sampling point of the transmission data from the position indicator 10 in the position detection device 20. The reception sampling point of the transmission data from the position indicator 10 in the position detection device 20 is a point in time a predetermined time after the end of the duration T2 of each data transmission synchronizing signal SYC. Accordingly, the control circuit 40 may, for example, measure time (perform clock counting) to detect a point in time later than the reception sampling point at which the predetermined time has passed after the end of the duration T2 of each data transmission synchronizing signal SYC, and make this point in time a timing point at which the signal level of the signal in the falling region of each of the multiple data transmission synchronizing signals SYC is to be forcibly reduced.

In this embodiment, however, the timing point at which the signal level of the signal in the falling region of each of the burst signal SB and the data transmission synchronizing signals SYC is forcibly reduced is simply set at a point in time at which the fall of the burst signal SB or data transmission synchronizing signal SYC is detected. As described above, the point in time at which the fall of each of the burst signal SB and the data transmission synchronizing signals SYC is detected is a point in time at which the envelope detection output DET is decreased beyond the threshold level Vth. Accordingly, as shown in FIG. 4C and FIG. 5C, the threshold level Vth is set to such a level that the fall of the data transmission synchronizing signal SYC will be detected at a point in time after the reception sampling point of the transmission data from the position indicator 10 in the position detection device 20, and after the end of the duration T2 of the data transmission synchronizing signal SYC. Here, FIG. 4D and FIG. 5D each illustrate a timing signal TG having information as to points in time at which the burst signal SB rises and falls and each data transmission synchronizing signal SYC rises and falls, on the basis of the envelope detection output DET from the detector circuit 30.

As illustrated in FIGS. 5C to 5G, in the position indicator 10 according to this embodiment, the control circuit 40 generates a switch control signal SW1 (see FIG. 5F) to turn on and keep the switch circuit 12 in the ON state for the predetermined time tin synchronization with the fall of the timing signal TG shown in FIG. 5D, thus controlling the switch circuit 12 to be turned on and kept in the ON state to forcibly reduce the signal level of the signal in the falling region of each of the burst signal SB and the data transmission synchronizing signals SYC.

Figure 6:
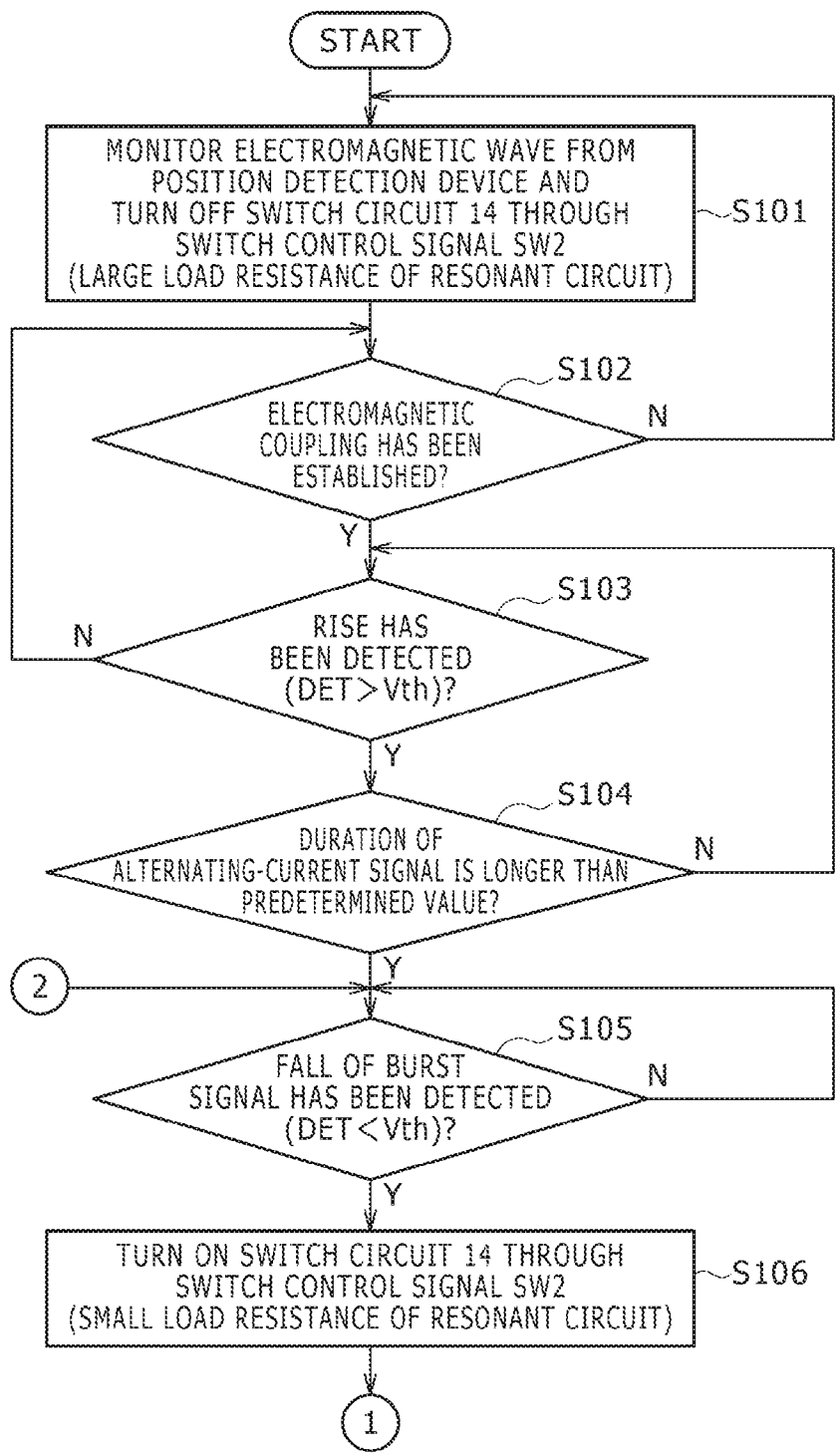
FIG. 6 is a diagram illustrating a portion of a flowchart used for explaining the operation of the position indicator according to an embodiment of the present disclosure.
Figure 7:
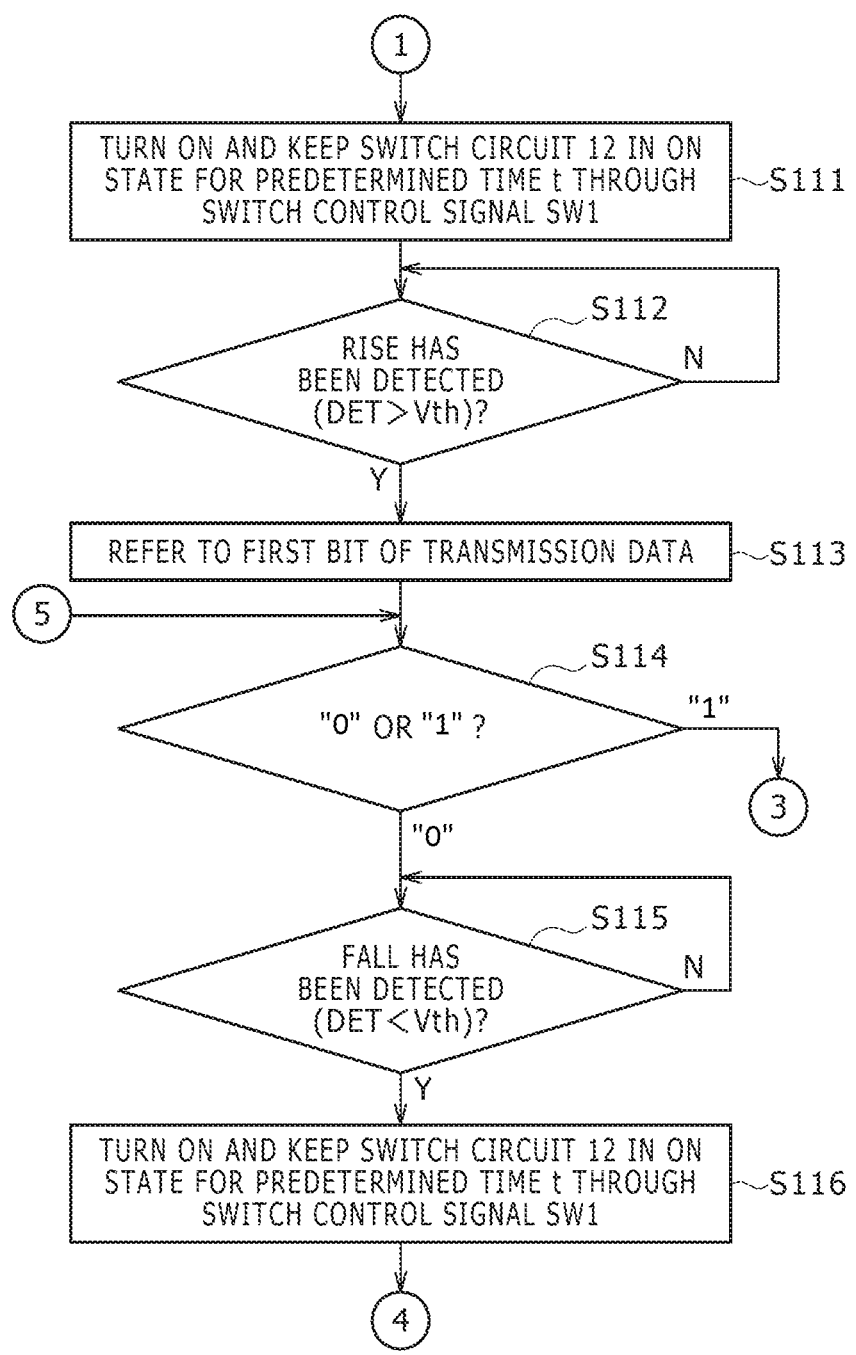
FIG. 7 is a diagram illustrating a portion of the flowchart used for explaining the operation of the position indicator according to an embodiment of the present disclosure.
Figure 8:
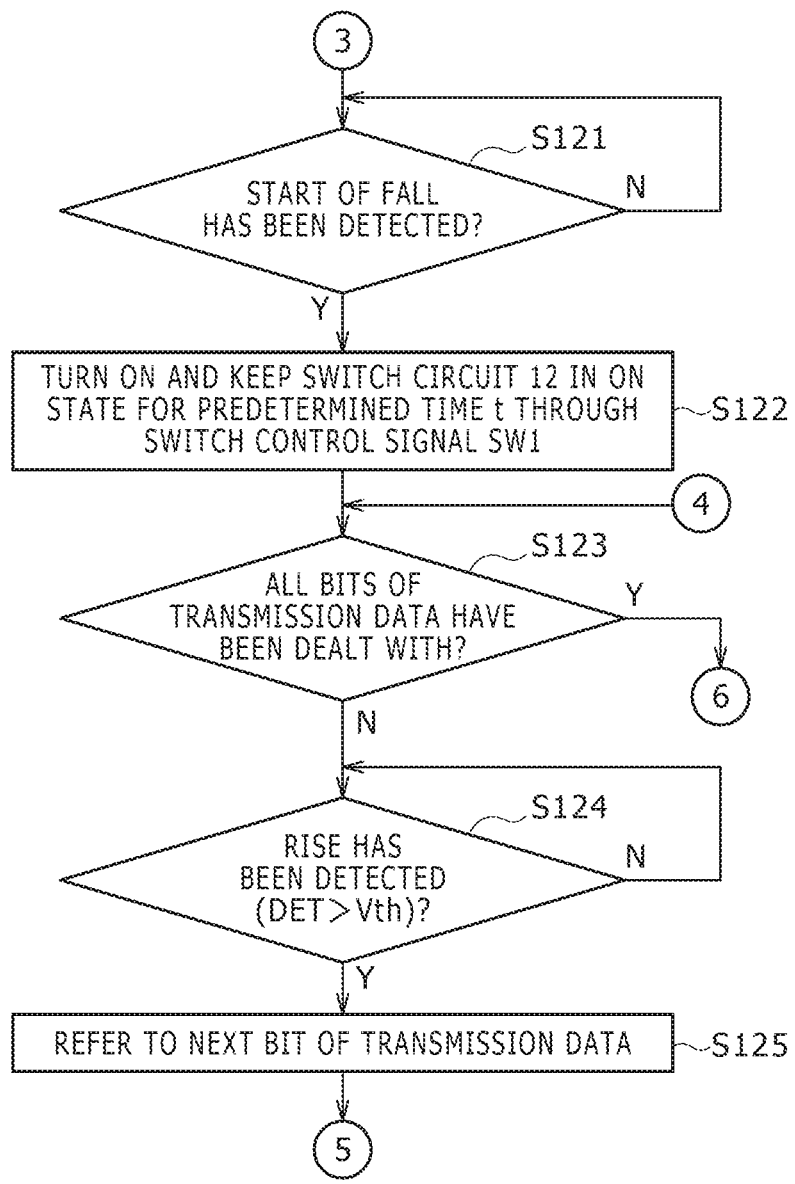
FIG. 8 is a diagram illustrating a portion of the flowchart used for explaining the operation of the position indicator according to an embodiment of the present disclosure.

Returning to the description of the flowcharts, if it is determined at step S105 in FIG. 6 that a fall of the burst signal SB has been detected, the control circuit 40 switches the switch circuit 14 to the ON state to reduce the load resistance value of the resonant circuit 11 to a smaller value at step S106, and causes the switch control signal SW1 (see FIG. 5F) to be at a high level for the predetermined time t to turn on and keep the switch circuit 12 in the ON state for the predetermined time t, to forcibly reduce the signal level of the signal in the falling region of the burst signal SB stored in the resonant circuit 11 (step S111 in FIG. 7).

Next, the control circuit 40 waits for a detection of a rise of the first data transmission synchronizing signal SYC after the burst signal SB (step S112), and if it is determined that the rise of the data transmission synchronizing signal SYC has been detected, the control circuit 40 refers to the first bit of the transmission data held in the buffer memory (step S113). Then, the control circuit 40 determines whether the bit referred to is "0" or "1" (step S114).

If it is determined at step S114 that the bit referred to is "0," the control circuit 40 monitors whether a fall of this data transmission synchronizing signal SYC has been detected (step S115), and if it is determined that the fall has been detected, the control circuit 40 causes the switch control signal SW1 (see FIG. 5F) to be at a high level for the predetermined time t to turn on and keep the switch circuit 12 in the ON state for the predetermined time t, to forcibly reduce the signal level of the signal in the falling region of the burst signal SB stored in the resonant circuit 11 (see the first, second, and fourth data transmission synchronizing signals SYC in FIG. 5C) (step S116).

Next, after step S116, the control circuit 40 determines whether transmission processes have been completed with respect to all the bits of the transmission data (step S123 in FIG. 8), and if it is determined that the transmission processes have not been completed with respect to all the bits of the transmission data, the control circuit 40 waits for a detection of a rise of the next data transmission synchronizing signal SYC (step S124), and if it is determined that the rise of the next data transmission synchronizing signal SYC has been detected, the control circuit 40 refers to the next bit of the transmission data held in the buffer memory (step S125). Then, the control circuit 40 returns control to step S114 in FIG. 7 after step S125, and repeats the step S114 and subsequent steps.

Figure 9:
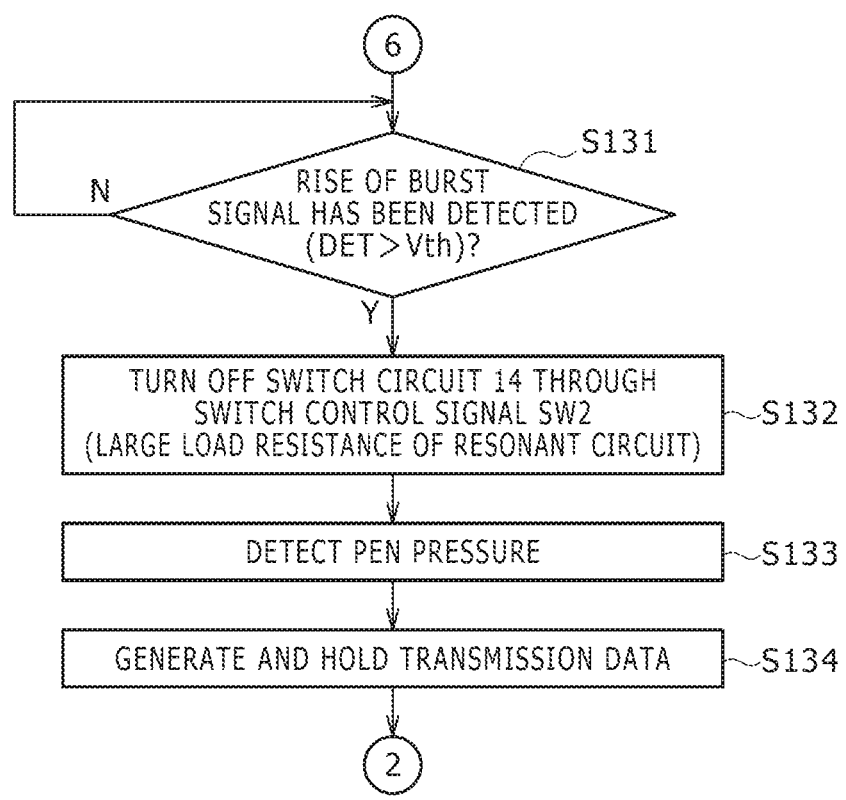
FIG. 9 is a diagram illustrating a portion of the flowchart used for explaining the operation of the position indicator according to an embodiment of the present disclosure.

Meanwhile, if it is determined at step S123 that the transmission processes have been completed with respect to all the bits of the transmission data, the control circuit 40 waits for a detection of a rise of the next burst signal SB (step S131 in FIG. 9).

If it is determined at step S131 that the rise of the burst signal SB has been detected, the control circuit 40 turns off the switch circuit 14 through the switch control signal SW2 to cause the load resistance value of the resonant circuit 11 to be large (theoretically, infinitely large) (step S132).

During the duration T1 of the burst signal SB, the control circuit 40 performs a process of detecting the pen pressure (step S133). More specifically, as described above, the variable capacitor 71 the capacitance of which varies in accordance with the value of the pen pressure is charged, and is thereafter caused to discharge through the resistor 72, and a time required for the voltage across the variable capacitor 71 to reach a predetermined voltage is measured. Then, the control circuit 40 generates transmission data corresponding to the value of the pen pressure on the basis of the measured time, and holds the generated transmission data in the buffer memory (step S134).

Then, after step S134, the control circuit 40 returns control to step S105 in FIG. 6, and repeats step S105 and subsequent steps.

As described above, in the position indicator 10 according to this embodiment, the signal level of a signal after the reception sampling point in the position detection device 20 within the signal in the falling region of each data transmission synchronizing signal SYC is forcibly reduced regardless of the value of the corresponding bit of the transmission data, and this allows the transmission period of each bit of the transmission data to be the period Pb (see FIG. 5B), which is even shorter than the period Pa (see FIG. 4B) in the case of FIGS. 4A to 4F. This makes it easier to satisfy a demand for an increased number of bits of transmission data in the position indicator 10.

In addition, the signal level of the signal in the falling region of the burst signal SB is also forcibly reduced, and this leads to further shortening the repeat period of the cycle composed of the burst signal SB and the multiple data transmission synchronizing signals SYC.

Further, the reduction in the signal level of the signal in the falling region of each of the burst signal SB and the data transmission synchronizing signals SYC eliminates the need for a time adjustment according to the signal level of the signal in the falling region, and this increases flexibility in designing the position indicator 10 and the position detection device 20.

[Example Modifications of Embodiment Described Above]

In the above-described embodiment, the burst signal SB, which serves as a basis, is detected on the basis of the duration of the alternating-current signal; the point in time of the rise of the subsequent burst signal is detected on the basis of the fact that the number of data transmission synchronizing signals SYC is equal to the number corresponding to the predetermined number of bits of the transmission data; and the timing point at which the load resistance value of the resonant circuit 11 is switched to the greater value is a point in time at which the envelope detection output DET at the point in time of the rise exceeds the threshold value. Note, however, that the timing point at which the load resistance value of the resonant circuit 11 is switched to the greater value is not limited to the above timing point.

For example, it may be so arranged that: the duration of the alternating-current signal is constantly monitored; it is determined whether the duration of the alternating-current signal is longer than the duration of the alternating-current signal in the case of the data transmission synchronizing signal SYC; if it is determined that the duration of the alternating-current signal is longer than the duration of the alternating-current signal in the case of the data transmission synchronizing signal SYC, it is determined that the alternating-current signal is an alternating-current signal of a section of the burst signal SB; and at the time of this determination, the load resistance value of the resonant circuit 11 is switched to the greater value.

Further, the timing point at which the load resistance value of the resonant circuit 11 is switched from the greater value to the smaller value may not necessarily be the point in time at which the envelope detection output DET of the burst signal decreases beyond the threshold value, but may be any point in time that allows a fall of the burst signal to be recognized.

Still further, in the above-described embodiment, the timing point at which the signal level of the signal in the falling region of each of the burst signal SB and the data transmission synchronizing signals SYC is reduced is determined by comparing the envelope detection output DET corresponding to the electromagnetic wave received by the resonant circuit 11 with the predetermined threshold value. Here, in the above-described embodiment, the same threshold level Vth is used for both the burst signal SB and the data transmission synchronizing signals SYC, but different threshold levels may alternatively be used for the burst signal SB and the data transmission synchronizing signals SYC.

Still further, as described above, the timing point at which the signal level of the signal in the falling region of each of the burst signal SB and the data transmission synchronizing signals SYC is reduced may be determined through time measurement to be a point in time a predetermined time after the start of the fall of the burst signal SB or the data transmission synchronizing signal SYC. Here, the predetermined time from the start of the fall to the timing point at which the signal level is reduced may differ between the burst signal SB and the data transmission synchronizing signal SYC.

Still further, in the above-described embodiment, the load resistance value of the resonant circuit is switched by turning on or off the switch circuit 14 to connect or disconnect one resistor to or from the resonant circuit 11. Note, however, that a resistor connected to the resonant circuit may be switched between a first resistor having a large resistance value and a second resistor having a resistance value smaller than that of the first resistor by turning on and off a switch circuit.

Still further, it may be so arranged that a first resistor is connected in parallel with the coil of the resonant circuit, and a series circuit composed of a switch circuit and a second resistor is connected in parallel with the first resistor, so that the second resistor can be connected in parallel to or disconnected from the first resistor by turning on or off the switch circuit to vary the load resistance value of the resonant circuit and to configure the resonant circuit to have desired resonance characteristics.

Still further, although the charge storage capacitor is used as a storage element provided in the position indicator 10 according to the above-described embodiment, a rechargeable secondary battery, such as, for example, a lithium-ion battery, may alternatively be used.

It is to be noted that the present disclosure is not limited to the foregoing embodiment, and that various changes can be made without departing from the spirit of the present invention.

What is claimed is:

1. A position indicator comprising:
   a resonant circuit which, in operation, receives electromagnetic waves transmitted intermittently from a position detection device with a first duration and a second duration, the second duration being shorter than the first duration; and
   a load resistance value control circuit which, in operation, controls a load resistance of the resonant circuit such that different values of the load resistance are set for the first duration and the second duration, a value of the load resistance set for the second duration being smaller than a value of the load resistance set for the first duration,
   wherein the load resistance value control circuit includes:
      a first switch which, in operation, switches between a first state in which both ends of a coil of the resonant circuit are shorted, and a second state in which the ends of the coil of the resonant circuit are not shorted, and
      a series circuit including a resistor and a second switch, wherein the second switch, in operation, switches between a first state in which the resistor and the second switch are connected in parallel with the resonant circuit, and a second state in which the resistor and the second switch are not connected in parallel with the resonant circuit, and wherein the resonant circuit, in operation, transmits a signal when the first switch is switched between the first and second states while the second switch is switched to and remains in the first state.

2. The position indicator according to claim 1, wherein the load resistance value control circuit, in operation, controls the second switch to be in the second state for the first duration, and to be in the first state for the second duration.

3. The position indicator according to claim 2, wherein the load resistance value control circuit, in operation, controls the second switch to be in the first state or the second state at a timing corresponding to the first duration of the electromagnetic waves received from the position detection device.

4. The position indicator according to claim 1, further comprising:
an information generating circuit which, in operation, generates information to be transmitted to the position detection device,
wherein the load resistance value control circuit, in operation, controls one or more characteristics of the resonant circuit in accordance with the information generated by the information generating circuit at a timing corresponding to the second duration of the electromagnetic waves received from the position detection device, and transmits the information generated by the information generating circuit to the position detection device using the signal.

5. The position indicator according to claim 4, wherein the load resistance value control circuit, in operation, controls the first switch to turn be in the first state and the second state in accordance with the information generated by the information generating circuit, and transmits the information generated by the information generating circuit to the position detection device using the signal.

6. The position indicator according to claim 5, wherein the load resistance value control circuit, in operation, controls the first switch to be in and remain in the first state for a predetermined time to short the ends of the coil, at a predetermined timing after the information generated by the information generating circuit is received by the position detection device.

7. The position indicator according to claim 6, wherein at a transmission end of the first duration of the electromagnetic waves transmitted from the position detection device, the load resistance value control circuit controls the first switch to be in and remain in the first state for the predetermined time to short the ends of the coil.

8. The position indicator according to claim 4, wherein the information generated by the information generating circuit is information regarding a pressure applied to a tip portion of the position indicator.

9. A position indicating method comprising:
receiving, by a resonant circuit, electromagnetic waves transmitted intermittently from a position detection device with a first duration and a second duration, the second duration being shorter than the first duration; and
controlling a load resistance of the resonant circuit, the controlling including setting different values of the load resistance for the first duration and the second duration, a value of the load resistance set for the second duration being smaller than a value of the load resistance set for the first duration,
wherein the load resistance value control circuit includes:
a first switch which, in operation, switches between a first state in which both ends of a coil of the resonant circuit are shorted, and a second state in which the ends of the coil of the resonant circuit are not shorted; and
a series circuit including a resistor and a second switch, wherein the second switch, in operation, switches between a first state in which the resistor and the second switch are connected in parallel with the resonant circuit, and a second state in which the resistor and the second switch are not connected in parallel with the resonant circuit, and
transmitting a signal from the resonant circuit, the controlling of the load resistance of the resonant circuit including switching the first switch between the first and second states to transmit the signal, and switching the second switch to the second state and keeping the second switch in the first state while the switching of the first switch is performed.

10. The position indicating method according to claim 9, wherein the controlling of the load resistance includes controlling the second switch to turn off for the first duration and to turn on for the second duration.

11. The position indicating method according to claim 10, wherein the controlling of the load resistance includes controlling the second switch to turn on or off at a timing corresponding to the first duration of the electromagnetic waves received from the position detection device.

12. The position indicating method according to claim 9, further comprising:
charging a charge storage circuit using the electromagnetic waves transmitted from the position detection device and received by the resonant circuit; and
operating a resonance characteristic control circuit using a stored voltage from the charge storage circuit as a power supply voltage, the controlling of the load resistance being performed by the resonance characteristic control circuit.

* * * * *